(12) United States Patent
Diakonov et al.

(10) Patent No.: US 7,062,958 B2
(45) Date of Patent: Jun. 20, 2006

(54) RECEPTACLE FOR SAMPLING DOWNHOLE

(75) Inventors: Igor Igorevitch Diakonov, Moscow (RU); Anthony Robert Holmes Goodwin, Cambridge (GB); Andrew Loris Kurkjian, Sugar Land, TX (US); Jonathan Webster Brown, Dunecht (GB); John Allan Nighswander, Scotland (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/205,644

(22) Filed: Jul. 25, 2002

(65) Prior Publication Data

US 2003/0033866 A1 Feb. 20, 2003

(30) Foreign Application Priority Data

Jul. 27, 2001 (GB) .................................. 0118321.9

(51) Int. Cl.
*E21B 49/00* (2006.01)
*E21B 47/00* (2006.01)
(52) U.S. Cl. .................................. 73/152.23; 166/264
(58) Field of Classification Search ............. 73/152.55, 73/152.18, 152.23, 152.33; 166/264; 175/50, 175/53
See application file for complete search history.

(56) References Cited

U.S. PATENT DOCUMENTS

| 4,535,843 A | 8/1985 | Jageler |
| 4,573,532 A | 3/1986 | Blake |
| 4,635,717 A | 1/1987 | Jageler |
| 5,289,875 A * | 3/1994 | Stokley et al. ............... 166/264 |
| 5,329,811 A | 7/1994 | Schultz et al. |
| 5,337,822 A * | 8/1994 | Massie et al. ............... 166/264 |
| 5,337,838 A * | 8/1994 | Sorensen ...................... 175/59 |
| 5,341,100 A | 8/1994 | Taylor |
| 5,351,532 A * | 10/1994 | Hager ...................... 73/152.55 |
| 5,473,939 A | 12/1995 | Leder et al. |
| 5,549,162 A | 8/1996 | Moody et al. |

(Continued)

FOREIGN PATENT DOCUMENTS

EP 0 095 837 12/1983

(Continued)

OTHER PUBLICATIONS

Schlumberger WFAS-S Wellsite Fluid Analysis System Schlumberger internal document SMP-6049 (Sep. 1997).

(Continued)

*Primary Examiner*—Hezron Williams
*Assistant Examiner*—John Fitzgerald
(74) *Attorney, Agent, or Firm*—Jody Lynn DeStefanis; Steven Gahlings; William L. Wang (57) ABSTRACT

A receptacle (10) for use in collecting samples down a well bore (14) is provided, the receptacle comprising a plurality of interconnecting modules (22, 24, 26, 30, 32, 34). A main chamber (22) is capable of holding a sample, and sensors (58, 60, 62, 64) within the chamber detect physical and chemical characteristics of the sample. Valves (50, 52) in a chamber wall seal the chamber (22) after a fluid sample has been collected. A communication means is placed in communication with the chamber (22) so as to provide an externally accessible port which communicates with the inside of the chamber (22) and allows detection and analysis of sample characteristics without removing the sample from the sealed chamber (22). The chamber (22) includes a piston (82) which is adjustable to keep pressure constant in the chamber and a heating element (58) to keep temperature constant. A method for sampling downhole fluids is also provided.

24 Claims, 4 Drawing Sheets

U.S. PATENT DOCUMENTS

| | | | |
|---|---|---|---|
| 5,609,205 A | | 3/1997 | Massie et al. |
| 5,622,223 A | | 4/1997 | Vasquez |
| 5,635,631 A | | 6/1997 | Yesudas et al. |
| 5,799,733 A | * | 9/1998 | Ringgenberg et al. ...... 166/264 |
| 5,803,186 A | * | 9/1998 | Berger et al. ................. 175/50 |
| 5,868,201 A | * | 2/1999 | Bussear et al. ................ 166/53 |
| 5,887,652 A | * | 3/1999 | Beck et al. ................... 166/264 |
| 5,901,788 A | | 5/1999 | Brown et al. |
| 5,934,374 A | * | 8/1999 | Hrametz et al. ............ 166/264 |
| 5,992,250 A | | 11/1999 | Kluth et al. |
| 6,026,915 A | * | 2/2000 | Smith et al. ................... 175/50 |
| 6,157,893 A | * | 12/2000 | Berger et al. ................... 702/9 |
| 6,178,815 B1 | * | 1/2001 | Felling et al. ........... 73/152.19 |
| 6,334,489 B1 | * | 1/2002 | Shwe et al. ............ 166/250.01 |
| 6,343,507 B1 | * | 2/2002 | Felling et al. ........... 73/152.19 |
| 6,439,306 B1 | * | 8/2002 | Patel ........................... 166/264 |
| 6,439,307 B1 | * | 8/2002 | Reinhardt .................... 166/264 |
| RE38,129 E | * | 6/2003 | Kleinberg ................ 73/152.18 |
| 6,612,156 B1 | * | 9/2003 | Hakimuddin ............... 73/61.75 |
| 6,629,451 B1 | * | 10/2003 | Taylor ....................... 73/54.28 |
| 6,688,390 B1 | * | 2/2004 | Bolze et al. ................. 166/264 |
| 6,702,017 B1 | * | 3/2004 | Corrigan et al. ............ 166/264 |
| 6,761,062 B1 | * | 7/2004 | Shapiro ................... 73/152.41 |

FOREIGN PATENT DOCUMENTS

| | | |
|---|---|---|
| EP | 0 295 923 A2 | 12/1988 |
| EP | 1 045 113 | 10/2000 |
| GB | 2 215 845 | 9/1989 |
| GB | 2 252 296 | 8/1992 |
| GB | 2 348 222 | 9/2000 |
| GB | 2348222 A * | 9/2000 |
| WO | WO 200034624 A2 * | 6/2000 |

OTHER PUBLICATIONS

Schlumberger Sampling Wireline formation testing and sampling, Houston, Texas, 1996, pp. 10-1 to 10-25.

Baker Atlas Reservoir Characterization Instrument (RCI) /http://www.bakerhughes.com/bakeratlas/ reservoir_production/rci/index.htm.

Wallace et al A distributed optical fibre fluorosensor for pH measurement Journal of Luminescence, vol. 72-74, 1997, pp. 1017-1019.

* cited by examiner

RECEPTACLE FOR SAMPLING DOWNHOLE

FIELD OF THE INVENTION

This invention relates to a receptacle for sampling fluid in a well bore, and to a method of obtaining a fluid sample. In particular, this invention relates to a receptacle having sensors which can monitor chemical and physical properties of the sample.

BACKGROUND TO THE INVENTION

Sampling of fluids within a well bore is becoming increasingly important as evaluation and development of a reservoir depends on the properties of the fluid in the reservoir. Downhole samples of the fluid are preferred to samples taken at the surface as they better represent downhole fluid properties. Fluid samples taken at the surface can have significantly different properties to a downhole sample due to variations in temperature and pressure that occur as the fluid travels to the surface and at the surface. Existing tools for downhole fluid sampling include a wireline conveyed sampling bottle which acquires a single sample downhole and is retrieved from downhole to surface. Wireline (coil tubing run) tools which are capable of pumping fluids from a borehole and from a reservoir formation into sampling chambers can also be used.

Once samples have been taken and placed within a sample bottle, the subsequent transport of the sample to a laboratory can cause irreversible changes in the sample which will alter its properties, and limit its usefulness in assessing actual downhole properties of the reservoir fluid. For example, often the sample is transferred from a sample bottle to another suitable container for transport. Variations in conditions surrounding the container during transport will affect the sample and its properties. Also the sample must be transferred out of the container once the laboratory is reached and again this can affect the sample.

SUMMARY OF THE INVENTION

The present invention aims to provide an apparatus and method for sampling fluid in a well bore.

According to the invention an apparatus is provided for analysing fluid from a subterranean formation, the apparatus comprising a chamber adapted for deployment in a wellbore and to enclose and hold a sample of fluid; and a sensor adapted to sense at least one characteristic of fluid within the chamber while downhole.

As used herein the term "fluid" refers to either gas or liquid.

A communication means is preferably placed within a wall of the chamber so as to provide an externally accessible port which communicates with the inside of the chamber, but yet is sealed so as to ensure the seal of the chamber is not compromised. Communication can be carried out in various methods, for example via a cable (cable port) for real-time down hole or surface exchange. Alternatively a plug in port (or and remotely interrogated port) could be used. Alternatively, optical windows can be used for visual inspection.

The chamber preferably further comprises a fluid conduit sealable by the sealing means, such as first and second valves placed at either end of the conduits and which open to allow fluid to pass through the chamber, and are shut to seal the chamber after a suitable sample has been acquired. Sometimes the downhole fluid is contaminated, for example with drilling mud, and in the contaminated state does not truly represent the characteristics of fluid from a reservoir of interest. Having a fluid conduit allowing through flow of fluid allows a sample to be selected once non-contaminated fluid is flowing through the chamber. Typically the sensing means actively samples the fluid properties to determine when there is no contamination present, at which point the valves are closed to trap a sample within the chamber.

According to another embodiment, the fluid flows through a separate chamber, external to the bottle, where the contamination is assessed prior to filling the sample collection vessel. The vessel can also be used as a downhole PVT laboratory in this case the sample would be collected, analysed and expunged before returning the tool to surface empty. Thus a type of emission free testing can be provided.

The apparatus may include a plurality of sensors each capable of detecting and analysing a characteristic of the sample. Thus the apparatus may comprise sensors which detect and analyse temperature, pressure, physical properties and chemical properties of the sample.

The chamber may further comprise means for altering pressure and means for altering temperature, where the communication means monitors temperature and pressure readings from the sensing means and adjusts the means for altering pressure and the means for altering temperature to keep pressure and temperature constant within the chamber. Typically the means for altering pressure is a piston within the chamber which alters the volume of the chamber as it moves to control pressure, with the means for altering temperature being a heating coil either external or internal to the chamber. The communication means is thus able to monitor and actively control the conditions within the chamber to ensure that the conditions under which the sample was acquired are maintained continuously, even after the receptacle is brought to surface from downhole. This ensures that the sample does not undergo irreversible changes relating to its characteristics as a result of subsequent changes in the temperature of the receptacles surrounding and thus pressure.

The apparatus may be adapted to be remotely interrogated so as to allow for information transfer and monitoring of conditions inside the chamber during transport of the receptacle and during storage of the receptacle.

The apparatus may also include a connector to connecting to a wireline. This allows the chamber to be lowered downhole on a wireline for collection of a sample and subsequently retrieved to surface.

The chamber may comprise a plurality of modules in mating engagement with the chamber, the modules containing analytical and processing equipment for analysis of a sample. By having an apparatus which is assembled from a series of modules and a chamber, the apparatus can be readily modified for different types of analysis as each module performs a different type of interaction with the sample in the main chamber. Thus, for example, the apparatus may comprise a main chamber with three minor compartments disposed at a lower end of the chamber and two further minor compartments disposed at an upper end of the chamber, the five minor compartments respectively containing analytical equipment, chemicals, sample treatment chamber, a spectrometer with a light source, and electronic processing devices. The apparatus may also have a means of varying the pressure such as a moveable piston.

The apparatus preferably communicates with a memory device to store information relating to the sample as a function of time for subsequent download. The memory device may be contained in a module attached to the chamber.

The chamber typically includes means for altering pressure and temperature and sensing means so that a self-contained unit is provided for holding the sample. The minor compartments or modules may contain chemicals for injecting into the main chamber when needed, with this injection being regulated by the communication means. These chemicals may be appropriate for removing gases such as $H_2S$ and $CO_2$ from the sample, or for calibration purposes, or to prevent precipitation of organic and mineral solids The apparatus may further comprise a stirring device located within the chamber, such as an acoustic transducer.

The chamber may be provided with optical windows within its walls, such as made of sapphire so that the contents of the chamber can be viewed when needed.

The receptacle thus provides integral sampling and analysis within one vessel and ensures that no transfer of sample outside the chamber is needed for analysis to take place. Thus a simple, small tool is provided which is particularly suitable for use downhole.

In accordance with another aspect of the invention, there is provided a method of sampling downhole fluids, comprising placing a chamber downhole; collecting at least one sample in the chamber; sealing the sample within the chamber; sensing at least the temperature and pressure of the sample in the chamber; and controlling the temperature and pressure of the sample in response to the sensed temperature and pressure.

BRIEF DESCRIPTION OF THE DRAWINGS

The invention will now be described, by way of example, and reference to the accompanying drawings in which.

DETAILED DESCRIPTION OF THE INVENTION

With conventional sampling bottles, the sample is transferred at least once before analysis of the sample is undertaken and the conditions within the chamber cannot be monitored or maintained during transport or storage of the sample. The sample bottle in accordance with the present invention preferably allows monitoring of the physical and chemical parameters of the sample in the chamber whilst undergoing transport, and allows testing of the physical and chemical properties of the sample in situ within the chamber without exposure of the sample to conditions different to those downhole.

Figure 1:
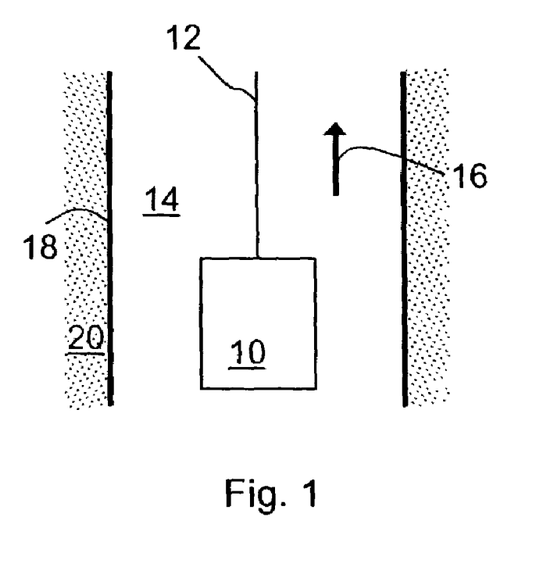
FIG. 1 shows a schematic diagram of a receptacle in accordance with the invention when placed downhole.

In FIG. 1, a receptacle 10 in accordance with the present invention is shown held on a wireline 12 within a cased well 14. Cased well 14 is defined by cased walls 18, outside of which is formation rock 20. Flow of fluid within the well bore is indicated by arrow 16. The receptacle 10 is in position ready to take a sample of downhole fluid so that the physical and chemical properties of the downhole fluid can be analysed to give information on the properties of the reservoir producing the fluid. The fluid being sampled is typically gas, or liquid hydrocarbons, or brine, or a mixture thereof. Once the sample is taken, the wireline with attached receptacle is retrieved from downhole to surface.

The receptacle, or sampling bottle, is capable of replicating and maintaining equivalent downhole conditions in an internal chamber where the sample is held, as discussed later. This ensures that once the sample is taken, it is kept stable at downhole conditions and physical and chemical changes that might occur to the sample during the trip to the surface and to a laboratory are prevented. The sample when analysed thus more accurately reflects the properties of downhole fluid.

The physical and chemical properties of the fluid which are of interest when assessing the reservoir include viscosity, density, bubble and dew point, wax, asphaltene, scale precipitation conditions, hydrate formation, chemical composition. It is important to avoid physical and chemical changes to the sample as many of these changes are irreversible or effectively irreversible, and will alter the sample properties. Effectively irreversible changes are those which in principle are thermodynamically irreversible but the kinetics of achieving equilibrium are so slow that it is not practical to reverse the change fully.

Where irreversible or effectively irreversible changes have occurred to the sample before analysis, the initial chemical and physical state of the sample, i.e. as in the reservoir, will generally not be precisely reconstructed even if the sample is put under reservoir temperature and pressure conditions during analysis. The sample properties will then not reflect downhole fluid properties. Hence, for practical purposes it is always best to avoid any chemical or physical changes to the fluid sample prior to analysis whether the change is considered to be reversible or not. Examples of various changes that can occur with reservoir fluids are summarized below:

1. Organic solids precipitation, for example asphaltenes and waxes, due to pressure and temperature drop;

2. Degassing of a sample, for example, arising from the (fluid) liquid pressure falling below the bubble pressure and the evolved gas escaped, perhaps through a seal;

3. Mineral precipitation (barite, calcite) due to temperature and/or pressure drop and degassing;

4. Loss of gases (mainly $H_2S$, but also $CO_2$) because of corrosion/reaction with sampling bottle;

5. Formation of gas hydrates;

6. Vapour-liquid phase separation;

7. Changes in pH; and

8. Other chemical and physical changes.

Figure 2:
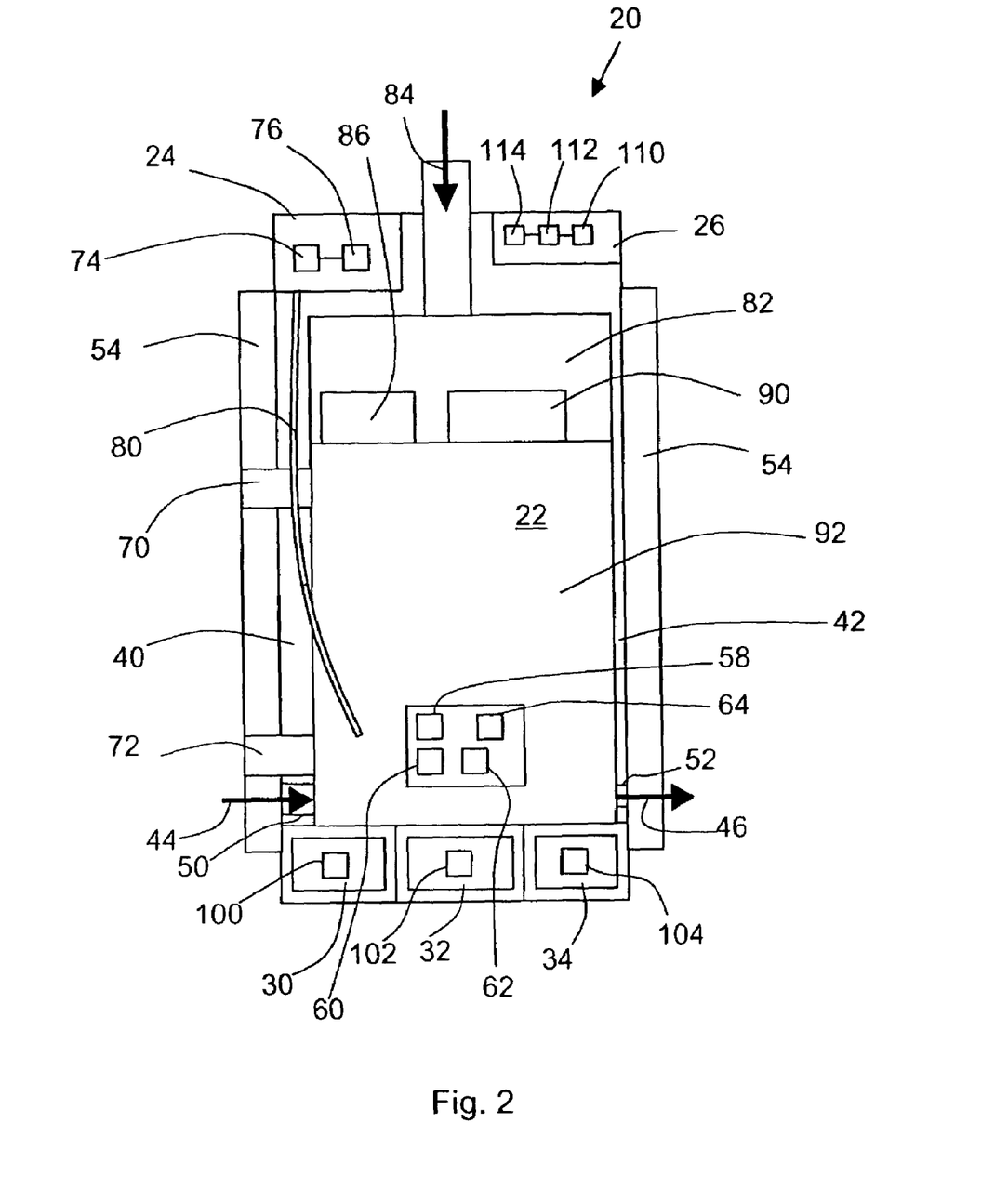
FIG. 2 shows a schematic drawing of a receptacle in accordance with the invention.

The cylindrical sampling bottle of around 1 m in length is shown in detail in FIG. 2. The bottle 20 is preferably made from a high strength, corrosion-resistant steel alloy, such as Ni alloys or Ti alloys, and is of a thickness so as to withstand the extreme pressures downhole. Alternatively, other materials could be used such as Titanium and Molybdenum alloys. The bottle 20 comprises a main chamber 22 having an internal volume of preferably around 5–700 cc and five minor chambers 24, 26, 30, 32, 34 in mating engagement with main chamber 22 so as to form a composite unit for taking samples which is sealed except when acquiring a sample. This modular structure allows the minor chambers to be chosen according to the characteristics that one wishes to analyse and thus the bottle can be designed to give any combination of sensors and equipment within the main chamber 22 or the minor chambers 24, 26, 30, 32, 34 depending on the particular conditions downhole and the particular reservoir of interest and particular analyses needed down hole and on the surface. These analyses undertaken include, for example, formation water pH and resistivity, hydrocarbon physical (viscosity, density, refractive index, bubble/dew pressures) and chemical (chromatography) properties.

Towards the base of vertical walls 40, 42 of the main cylindrical chamber, there are provided two diametrically opposed apertures 44, 46 which are sealed with valves 50, 52. When the valves 50, 52 are opened, a passageway for conduit for through flow of fluid through the bottle is provided, with the valves 50, 52 being operable to close and thus shut the apertures once a sample is taken. An insulating jacket 54 surrounds the chamber 22, and this jacket 54 can also incorporate a heating coil, so as to heat the chamber 22 if so desired. A further heating element 58 is provided inside the chamber, together with selected sensors or devices 60, 62, 64.

In one vertical wall 40 of the chamber, there are provided two spaced apart optical windows 70 and 72, which extend inwards from the insulating jacket 54 to an inner face of the chamber. These optical windows are preferably made of sapphire so as to withstand the extreme pressures found downhole, and allow the contents of the chamber 22 to be viewed when on surface. Alternatively, other transparent materials could be used that are able to withstand the anticipated temperatures, pressures and sample chemistry. One of the modules 24 incorporates a light source 74 and a mini-spectrometer 76 and is provided with a fibre-optic cable 80 which passes into the interior of the chamber 22 so as to optically interrogate the interior of the chamber. Spectroscopic analysis of any sample within the chamber 22 can then be undertaken, with the fibre-optic cable being covered with chemicals allowing optical chemical interrogation of a sample, for example, to determine the pH. An array of light conducting glass substrates containing chemicals for providing chemical interrogation of a sample can also be present in the chamber, and responsive to light from the optical fibre. The optical fibre can also be used to determine physical properties of the fluid (for example, the formation of dew or bubbles arising from a phase transition).

A piston 82 supplied with hydraulic/electric power via a connector 84 is located within the chamber 22 and undergoes reciprocal movement along the chamber to alter the pressure within. An example of how piston operation can be achieved is discussed in U.S. Pat. No. 5,329,811. Temperature and pressure sensors 86, 90 are incorporated into the piston 82, as are certain physical and chemical sensors such as those responsive to pH, $H_2S$, acoustic waves and sensors to determine resistivity. All of these sensors are in contact with a fluid sample 92, once the sample is acquired.

Power is supplied to the connector 84 either by an outside power source such as wireline, for example when the bottle is downhole, or by a battery module, or any other external power source which can be plugged in to the connector.

Any particular combination of sensors and equipment can be used within the chambers 22, 24, 26, 30, 32, 34 to analyse physical and chemical properties of the sample, and the sensors and equipment discussed herein are exemplary combinations. The sample can thus be tested in a variety of different ways depending on the properties that need to be identified. U.S. Pat. Nos. 5,635,631 and 5,622,223 describe various ways of determining different characteristics of the fluid.

Some chemical sensors and miniaturized chemical analytical equipment (for example, Gas Chromatography (GC), liquid chromatography (LC), and mass spectrometry (MS)) are not in direct contact with the sampled fluid as they require sample preparation, but are held in the minor modules 30, 32, 34 where miniaturised sample treatment 100, separation 102 and pumping equipment 104 is located.

The various chemical sensors and chemical analytical equipment allow the following properties and information to be determined:

(i) Determine downhole sample chemistry needed for real-time reservoir evaluation.

(ii) Provide information for downhole sample validation. Thus the bottle allows contamination to be measured and this can be used to determine when the sample should be taken. Reservoir fluid is either continuously pumped through the chamber or intermittently sampled for these measurements.

(iii) Record the evolution of a sample containment conditions and in-bottle chemistry during the trip to the surface and to the laboratory.

(iv) Provide extra analytical possibilities on-rig on the surface and in the laboratory as extra modules with different chemical sensors/analytical equipment can be placed in communication with the main chamber 22. The bottle can thus act as a universal portable modular chemical laboratory which avoids any sample transfer once the sample has been acquired.

Where appropriate, specific chemicals are introduced into the chamber 22 for various purposes. These chemicals can be either introduced as liquids or as mixtures with polymers and retardation agents to ensure their continuous release and can either be placed in the bottle before it is placed downhole, or injected into the bottle when needed from minor auxiliary chambers/modules 30, 32 34. The contact of these chemicals with the sample 92 and the chemical and/or physical properties of the sample thereafter is recorded by sensors. The regulated injection of chemicals and recording of a sample's chemical "reply" to this injection can be used for downhole chemical analyses (titration) of a sample downhole. Specific chemicals can be introduced, for example, to:

(i) Absorb/remove aggressive gases (for example $H_2S$ and/or $CO_2$).

(ii) Provide an acidification to avoid mineral (for example carbonate) precipitation.

(iii) Inhibit mineral (barite) precipitation.

(iv) Calibrate chemical sensors. The bottle can be filled by a calibration solution to check sensors performance before being placed downhole (v) Calibrate physical sensors, for example density sensors.

Other sensors that can be used include acoustic transducers and acoustic sources to determine fluid phase transition and physical properties, such as bubble and dew point, wax and asphaltenes deposition. These sensors can be placed in the piston or in the wall of the chamber, or as a changeable, plug-in module. Acoustic measurements such as speed and attenuation of sound can be used for density and viscosity measurements.

Stirring devices 60, such as an acoustic transducer, can be located within the chamber and when operated avoid phase separation, i.e. heavy fractions precipitation.

Vibrating objects 62, such as a wire or plate, can also be fitted inside the chamber. These objects are used to determine density and viscosity of the fluid. Resistivity and capacitance (dielectric constant) sensors 64 can also be installed in the chamber, as can sensors for detecting multiple phase fluid volumes which can comprise optical, acoustic, or surface sensors along the chamber walls. Measurements of refractive index can be included, or example with the fibre optic cable 80, to give density. The fibre optic cable can also be used to transmit near infrared energy for chemical characterisation. This analysis preferably uses a neural network.

In FIG. 2, one of the modules 26 contains various electrical/electronic equipment for signal processing and signal transfer and the bottle thus has electrical processing equipment which is capable of storing data acquired by the sensors, instructing the modules to undertake analytical tasks, for example by releasing chemicals into the main chamber, providing remote readout of data stored within memory, and controlling temperature and pressure of the main chamber. Thus module 26 contains a signal converter block 110, which converts signals from physical and chemical sensors, or from equipment in the minor modules, and sends these converted signals to a microprocessor 112. The microprocessor records all data into a memory block 114.

The memory block 114 stores information from all sensors/equipment and also provides pre-programmed instructions to the sensors and equipment relating to the physical and chemical analysis that is to be conducted on the sample. Thus for some modules, the memory block 114 sends instructions to release chemicals into the main chamber 22, or tells the module to sample the fluid sample and then apply chemicals to a small amount of the fluid sample. All information on physical and chemical actions conducted upon the sample and all detected characteristics are held as a function of time. The memory 114 is readable through a cable and remotely interrogated by a scanner, and via a plug-in device linked to a computer. Thus a record of all data relating to the sample and its conditions is maintained and is readily accessible, covering the period from when the sample is acquired downhole, brought to surface, transported to a laboratory, and possibly stored for a long period of time.

Figure 5:
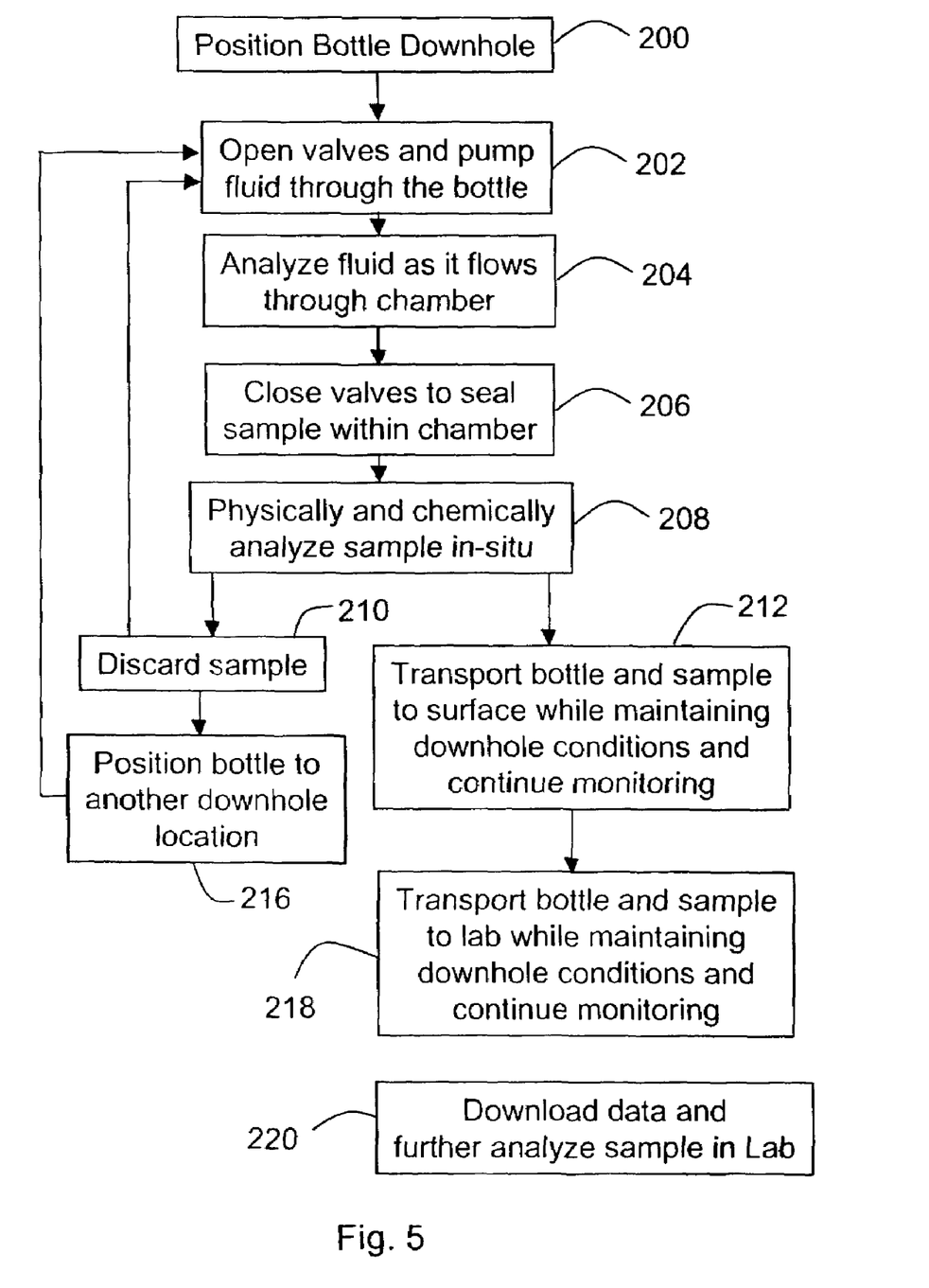
FIG. 5 is a flow chart showing various steps for acquiring a sample, according to a preferred embodiment of the invention.

FIG. 5 is a flow chart showing various steps for acquiring a sample, according to a preferred embodiment of the invention. In step 200, the bottle is placed downhole either on a wireline as in FIG. 1 or as part of a downhole tool as in FIG. 3. If desired, a plurality of bottles can be placed downhole spaced along a common wireline string or located within the same tool.

In step 202, once downhole and at the required sample depth, valves 50, 52 in the chamber 22 are opened and downhole fluid pumped through the bottle. In step 204, for the wireline conveyed bottle, the fluid can be analysed as it flows through the chamber to quantify contamination and to determine when to acquire a non-contaminated sample.

In step 206, the valves 50, 52 are then closed to seal a non-contaminated sample within the chamber 22 for subsequent analysis.

Figure 3:
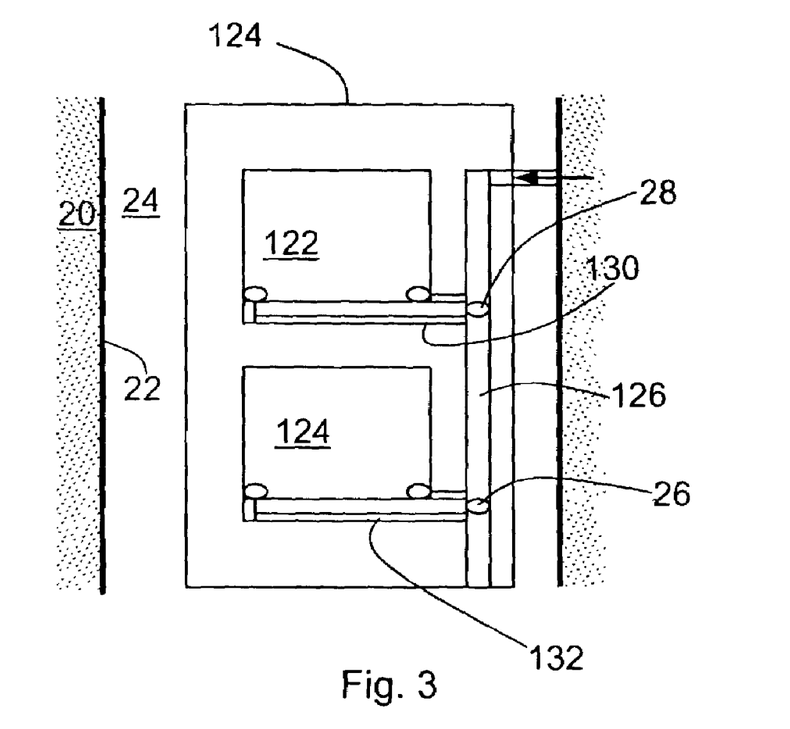
FIG. 3 shows a schematic diagram of two receptacles in accordance with the present invention when used within a downhole logging tool.

In FIG. 3, two bottles 120, 122 are placed within a downhole tool 124. Tool 124 is shown positioned in a wellbore 24 which is defined by borehole wall 22. Note that wellbore 24 is either a cased or open hole. Fluid is pumped through the bottles 120 and 122 using conduits 126, 130, and 132, and valves 26 and 28, until such time as a sample is acquired by closing off valves 50, 52. A clean-up curve can be generated from continuous readings of physical and chemical sensors in the chamber, or via analysing sampled and isolated portions of a fluid. This allows in-situ real time reservoir characterisation and to select when to sample to minimise contamination of the fluid.

Thus, the bottle is used to monitor continuously wellbore and reservoir (formation) fluid properties and the amount of contamination of the fluid with drilling mud. The bottle can also be used for zero-emission testing.

Referring again to FIG. 5, in step 208, once a sample is acquired, it is analysed physically and chemically in situ within the chamber 22 using any combination of physical and chemical sensors, chemical analytical equipment, and where desired chemical injection into the chamber and physical action upon the sample, such as change in temperature and/or pressure. After analysis, a sample is either discarded (step 210) or kept for subsequent laboratory study (step 212). The analysis of step 208 can be repeated either downhole or after the bottle is retrieved to surface, and can either be conducted continuously or as required.

As the sample is hermetically sealed within the main chamber and testing is possible without interfering with the seal, the sample integrity is maintained indefinitely. In step 212, the electrical processing equipment 110, 112, 114 continuously monitors conditions within the chamber using information received from sensors 86, 90, 60, 62, 64 and actively controls temperature and pressure by adjusting the amount of heating supplied by the thermal jacket and coil 58, and by adjusting the position of the piston 82 within the chamber 22 to alter the pressure. Thus the sample can be maintained at downhole conditions throughout its time within the chamber, ensuring that the sample accurately reflects the properties of the downhole fluid at all times as degradation of the sample due to fluctuations in temperature and pressure does not occur. Thus, the samples initial physical and chemical state is maintained.

In use, the chamber 22 is filled periodically with a calibration solution, such as before downhole deployment, during downhole job and during surface analyses. This allows the physical and chemical sensors and chemical analytical equipment in the bottle to be calibrated.

Instead of taking one sample and retrieving the bottle 20 to surface, in steps 210 and 216, the bottle can be used for performing multiple physical and chemical analyses on borehole and formation fluids in multiple downhole locations before taking sample(s) for retrieval to the surface. These analyses provide real-time downhole reservoir fluid description and detect the conditions of minimum sample contamination allowing acquisition of a sample with the best possible quality. Alternatively, after discarding the sample in step 210, another sample can be taken at the same location. In this way, a multisample mode is provided where multiple samples are taken at a location, for example 10 samples. The sampling can continue until a sample can be obtained having acceptable characteristics and then that sample can be transported to the surface.

When used in a flow through mode, or a multi-sample mode, the system can be used for emission free testing with a down hole drill stem tester (DHDST) or a modular formation dynamic tester (MDT).

In step 212, once a sample 92 has been collected in the chamber 22, the bottle is retrieved to surface and detached from the wireline or logging tool. The bottle allows continuous monitoring, analysis and control over physical and chemical properties of the sample during the journey to the surface (step 212) and to the laboratory (step 218) using the sensors, electrical processors and analytical equipment contained within the various modules forming the bottle. The pressure and temperature of the sample can thus be maintained as the sample travels from downhole to surface and then on to the lab.

At surface, the actions and analyses carried out upon the sample 92 can either be conducted using the modules used downhole, or minor modules 24, 30, 32, 34 can be replaced with modules containing different physical and chemical equipment or chemicals. On-site near wellbore and before detachment of the bottle from a tool, instructions are given to processor 112 for further regulation of temperature/sample chemistry and data recording within the chamber. If necessary, an external power source can be connected to the power connector 84.

During surface transfer of the bottle from the rig to the laboratory (step 218), the various elements contained in the modules in combination continuously monitor and control the physical and chemical properties of the sample. In step 220, once the sample reaches a laboratory, the whole history of the sample's physical and chemical properties is transferred to a corresponding laboratory file by interrogating the electrical processor/memory 112, 114 of the bottle. Various physical and chemical laboratory analyses are then performed directly in the chamber 22 using the bottle's temperature and pressure regulation ability together with chemical injections and by connecting additional modules where necessary. Alternatively the sample can be removed from the chamber for analysis, the sample history before reaching the laboratory being known as a result of the monitoring conducted whilst the sample was within the chamber.

Figure 4:
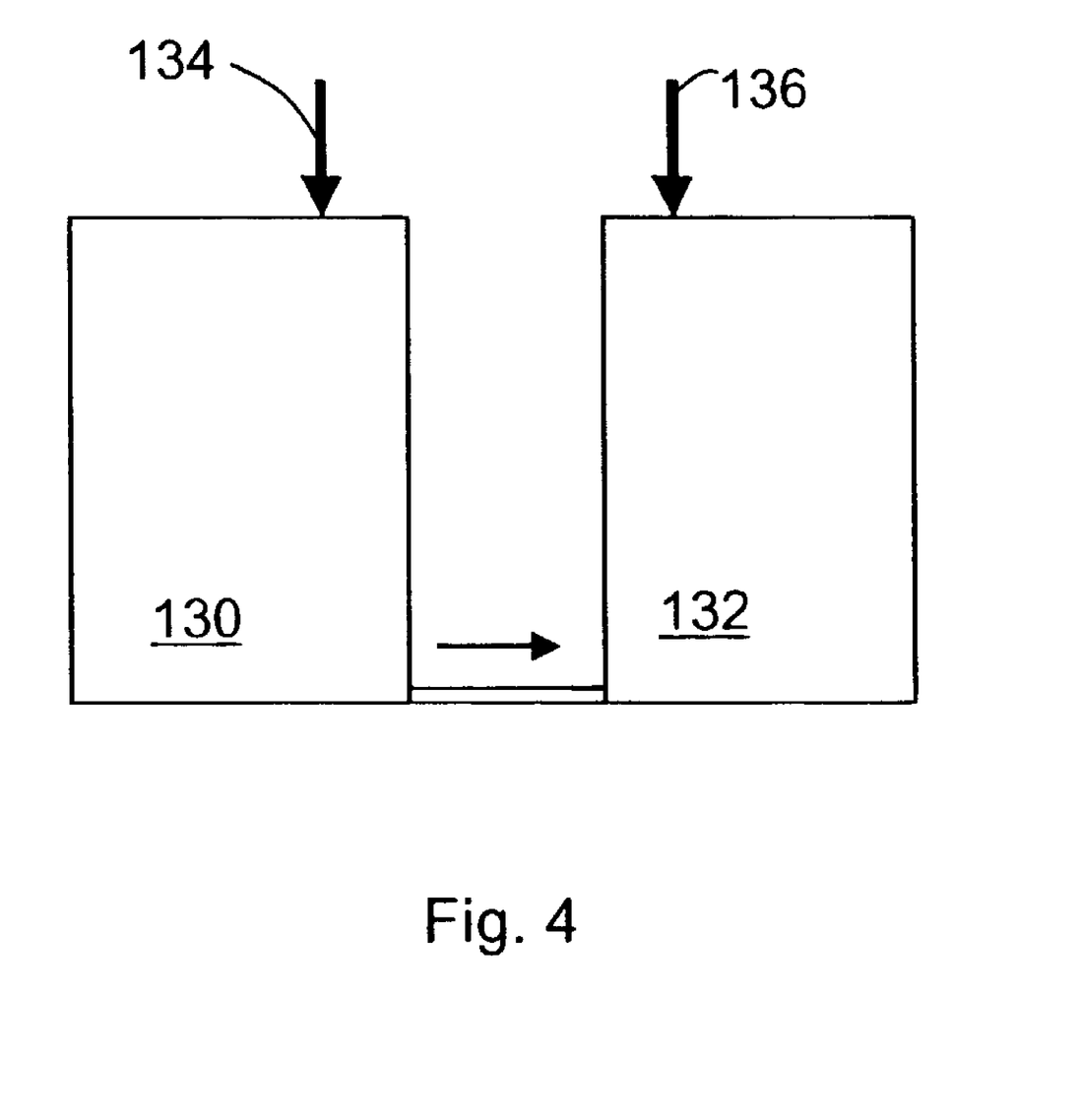
FIG. 4 shows a schematic diagram of sample transfer from a prior art sampling bottle to a receptacle in accordance with the present invention.

According to another embodiment of the invention, the bottle is used simply to convey samples from surface at a well to a laboratory. FIG. 4 shows the transfer of a downhole sample from a standard bottle 130 to a bottle 132 in accordance with the invention is shown schematically. Alternatively the bottle is used as part of an on-site (on-rig) portable physical and/or chemical laboratory for express analyses. Electrical and hydraulic power is applied to the bottle through connectors 134, 136. The bottle 132 allows the sample to be monitored continually during transport and storage and analysis can be conducted if necessary.

The bottle thus has a variety of different applications. In its more general form it provides a mini portable modular chemical/physical laboratory which allows analysis of a sample anywhere, avoiding the need to take the sample to a laboratory before analysis is undertaken.

The bottle can also act as an integrated transport and analysis vessel, when a sample is placed into the chamber when on surface. The bottle then monitors, records and controls sample conditions and analyses the sample during transport and/or storage.

In addition the bottle can act as an integral unit that acquires a sample, analyses a sample both downhole and on surface, and is a transport vessel. This ensures that a sample can be acquired, analysed and transported without any sample transfer between different containers. The sample integrity is thus maintained for as long a period as desired.

The above-described embodiments are illustrative of the invention only and are not intended to limit the scope of the present invention.

What is claimed is:

1. An apparatus for analyzing fluid from a subterranean formation, the apparatus comprising:
a receptacle configured for coupling with a wellbore deployment tool to provide for deployment of said receptacle in a wellbore penetrating said subterranean formation to collect a sample of said fluid and configured for uncoupling from said deployment tool to provide for storage or transport of said sample, said receptacle being adapted to enclose and hold said sample of fluid and to provide for detecting at least one of a physical property of said sample and a chemical property of said sample during storage or transport of said sample; wherein the receptacle comprises:
a chamber contained within said receptacle with one or more sealable apertures and configured to hold said sample, wherein said one or more sealable apertures are configured to provide for flow of the fluid into and out of the chamber; and
a sensor adapted to sense at least one chemical or physical characteristic of said sample within the receptacle during storage or transport of said sample in said receptacle.

2. The apparatus of claim 1, further comprising an electronic communication assembly placed within a wall of the chamber so as to provide an externally accessible port which communicates with the inside of the chamber, said communication assembly configured to provide for communication with the inside of the chamber during transportation or storage of the receptacle.

3. The apparatus of claim 1, further comprising a communication module coupled with the receptacle and adapted to provide for remote communication with the receptacle to allow for remote monitoring of conditions within the chamber during storage or transportation of the receptacle.

4. The apparatus of claim 1 further comprising a plurality of analyzing modules in mating engagement with the chamber, the modules containing analytical and processing equipment for analysis of a sample.

5. The apparatus of claim 1 further comprising a memory device coupled with the receptacle and configured to store information relating to the sample.

6. The apparatus of claim 1 further comprising a stirring device located within the chamber.

7. The apparatus of claim 1, wherein the chamber includes an optical window configured to provide visual access to the sample during transportation or storage of the receptacle.

8. The apparatus of claim 1, wherein the sensor analyses the fluid to determine when a sample is to be collected in the chamber.

9. The apparatus of claim 1, further comprising a plurality of sensors each capable of detecting and analyzing one or more of said at least one chemical or physical characteristic of the sample.

10. The apparatus of claim 9 wherein the plurality of sensors comprises a vibrator adapted to determine at least one physical property of the sample.

11. The apparatus of claim 1 further comprising one or more valves coupled with the one or more sealable apertures for sealing the chamber after a sample has been enclosed.

12. The apparatus of claim 11, wherein the one or more valves are operable to open at least one of the one or more sealable apertures to allow sampling of the downhole fluid and to close the at least one aperture to seal the chamber.

13. The apparatus of claim 1 further comprising a controller in communication with the sensor and adapted to actively control one or more characteristics of the sample during storage or transport of said sample in said receptacle in response to measurements from said sensor.

14. The apparatus of claim 13 further comprising an injector module for injecting a chemical into the chamber in response to signals from the controller.

15. The apparatus of claim 13 further comprising a heater to provide thermal energy to the sample in response to signals from the controller.

16. The apparatus of claim 15, wherein the controller actively controls the temperature of the sample within predetermined limits.

17. The apparatus of claim 13 further comprising a mechanical actuator adapted to exert physical action upon the sample in response to signals from the controller.

18. The apparatus of claim 17, wherein the mechanical actuator is adapted to alter pressure such that in combination with the controller the pressure is controlled within predetermined limits within the chamber.

19. A method of sampling downhole fluids, comprising:
coupling a receptacle with a wellbore deployment tool, wherein the receptacle contains a sampling chamber;
using the wellbore deployment tool to deploy the receptacle down a borehole;
collecting at least one sample in the sampling chamber;
sealing the receptacle thereby enclosing the sample within the sampling chamber;
sensing sampling conditions of the sample, wherein the sampling conditions comprise at least one of a chemical and a physical characteristic of the sample in the sealed receptacle when the sample is collected;
removing the receptacle from the borehole;
uncoupling the receptacle from the wellbore deployment tool;
sensing storage conditions of the sample, wherein the storage conditions comprise at least one of a chemical and a physical characteristic of the sample in the sealed receptacle when the sample is stored or transported in the receptacle; and
controlling the storage conditions of the sample in the sealed receptacle while storing or transporting the sample in the receptacle.

20. The method of claim 19 further comprising the steps of:
flowing the fluid through the chamber before said step of sealing; and
sensing one or more physical or chemical characteristics of the fluid during said step of flowing.

21. The method of claim 19 further comprising the step of controlling storage conditions of the sample in the sealed receptacle while performing the step of removing the receptacle from the borehole.

22. The method of claim 19 further comprising the steps of:
discarding the sample;
re-positioning the chamber to another downhole location; and
repeating said steps of collecting, sealing and sensing.

23. The method of claim 22 wherein said transporting the sample in the receptacle comprises transporting the chamber and sample to a laboratory.

24. The method of claim 22 wherein said storing the sample in the receptacle comprises storing the chamber and sample until said sample is analyzed.

* * * * *